US006142929A

United States Patent [19]

Padgett

[11] Patent Number: 6,142,929

[45] Date of Patent: Nov. 7, 2000

[54] SEXUAL STIMULATION APPARATUS

[76] Inventor: George Glenn Padgett, 106 English Manor, Guyton, Ga. 31312

[21] Appl. No.: 09/395,236

[22] Filed: Sep. 10, 1999

[51] Int. Cl.[7] ........................................................ A61F 5/00

[52] U.S. Cl. ................................ 600/38; 128/845; 601/49

[58] Field of Search .......................... 600/38–41; 601/46, 601/49, 51, 53, 54, 67, 69, 70; 128/845

[56] References Cited

U.S. PATENT DOCUMENTS

| | | | |
|---|---|---|---|
| 3,874,373 | 4/1975 | Sobel | 601/95 |
| 4,088,128 | 5/1978 | Mabuchi | 601/101 |
| 4,291,686 | 9/1981 | Miyashiro | 601/101 |
| 4,513,737 | 4/1985 | Mabuchi | 601/101 |
| 4,722,327 | 2/1988 | Harvey | 601/97 |
| 4,790,296 | 12/1988 | Segal | 600/38 X |
| 5,076,261 | 12/1991 | Black | 601/93 |
| 5,385,154 | 1/1995 | Fuhrman et al. | 128/845 |
| 5,389,062 | 2/1995 | Mitchum, Jr. | 600/38 |
| 5,453,080 | 9/1995 | Mitchum, Jr. | 600/38 |
| 5,676,637 | 10/1997 | Lee | 601/49 X |
| 5,725,473 | 3/1998 | Segal | 600/38 X |
| 5,851,175 | 12/1998 | Nickell | 600/38 |
| 5,875,779 | 3/1999 | Fuhrman et al. | 128/845 |

*Primary Examiner*—Samuel G. Gilbert
*Assistant Examiner*—Joseph A. Cadugan

[57] ABSTRACT

A sexual stimulation apparatus for the sexual gratification of a woman or man, by simulating vaginal or anal intercourse, which generally includes a long hollow box or tube; with a seat for two persons on top; inside the container mechanical levers and cranks powered by an electric gear reduction motor; an on/off switch; a power indicator light; a ground fault interrupt circuit; a rheostat; and a dildo mounted on the end of a lever which is positioned underneath the seat so the dildo extends through a hole in the seat and thrusts in a generally vertical motion. The rotational speed of the electric motor is reduced by a gear box and is further reduced by the rheostat. The gear box rotates a hub. The hub has a radially mounted bar. A short, generally vertical rod with ball joints on each end is the link between the end of the bar and the end of a horizontal lever. This configuration acts to convert the rotational motion of the motor into the vertical reciprocating motion of the lever. There is a ball bearing pivot point at the midpoint of the lever. The other end of the lever is attached loosely to a vertical tube. The opposite end of the tube consists of a clamping device that firmly holds the dildo. The commercially obtained, vibrating or non vibrating dildo, can be of various shapes, girths, lengths and textures, and may or may not be remotely controlled.

23 Claims, 5 Drawing Sheets

SEXUAL STIMULATION APPARATUS

BACKGROUND OF THE INVENTION

There exists a need for a cheap, effective, safe, private, disease free, non impregnating, and natural like way for a woman to achieve sexual gratification with a sexual stimulation apparatus. Not only do single women, but women married to impotent men deserve help. Many women have tried to masturbate and failed because of the same reason that one cannot tickle oneself This leaves a woman without a partner frustrated and can cause her to seek satisfaction that is not safe, disease free, non impregnating, or is immoral. Married women and single women who are attached to an impotent man are motivated to become unfaithful. Women may need to avoid traditional sexual intercourse because one half of the couple has an infectious disease. With A.I.D.S. (Acquired Immune Deficiency Syndrome) and numerous other sexually transmitted venereal diseases so prevalent in today's society, there are considerable risks involved in extramarital sex. Many women lose their partner to impotency or death while the woman still has sexual needs. This inventor found only three machines that attempt to provide relief for women. This invention is the first machine to use: ball joints on moving parts; a ground fault interrupt circuit; seats; wheels for moving the machine into position; a handle for pushing or pulling the machine into position; a vibrating dildo; rubber pads for vibration isolation; an adaptable dildo mounting assembly for mounting all lengths, textures, shapes, and girths of dildos (other patents use an automobile radiator hose clamp); a method of quickly disconnecting the dildo for easy cleaning; a power indicator light; a pivoting lever; vertical dildo thrusting instead of horizontal; no guide holes nor bushings to restrict the movement of the arm the dildo is fastened to; a flexible yet resilient arm to move the dildo; and the elimination of a wheel or pulley. This invention attaches a link directly to a hub on the gear box output shaft. The machine described in the application has been tested and is very effective. It simulates vaginal and anal intercourse. The users of this machine for achieving sexual satisfaction are: a woman alone; a woman with a male partner; a woman with a female partner; a man alone; or a man with a male partner. The vibrating dildo is commercially obtained and can be of various shapes, girths, lengths and textures. The dildo that has a remote battery pack with variable speed control attached with an electrical cord. Non remote controlled vibrating dildos and non vibrating dildos may also be attached to the tube. The rider sits on the seat with the dildo protruding through a hole in the seat. An electric motor powering a series of gears and levers causes the dildo to reciprocate in and out of the rider's vagina or anus. A partner may sit on the opposite seat to either operate the speed controls and/or provide further stimulation to the rider by kissing, hugging, and caressing. This apparatus has the primary purpose of providing the rider with sexual gratification and possibly an orgasm in the case of a female rider. A second purpose is to provide orgasm therapy or orgasm training. Women must learn to be orgasmic through experience and practice. Many women have never had an orgasm because they think it is dirty or their partner finishes the sex act before they achieve an orgasm. It can also be used before sex as a form of foreplay or after sex to achieve orgasm if the sex act did not achieve orgasm. A third purpose of the machine is to help impotent men achieve an erection for traditional sex by providing the male partner with visual and tactile stimuli from the rider of the machine.

BRIEF SUMMARY OF THE INVENTION

The invention is a sexual stimulation apparatus which is portable, enables the user to achieve sexual gratification and possibly an orgasm without exchanging body fluids with a partner, and is totally hygienic. The stimulation apparatus comprises, generally a motor situated within a container, the first end of a pivoting arm coupled to the motor and the second end attached to a generally vertical dildo which extends through the top of the container. The pivoting arm is coupled to the motor in a manner translating the rotational motion of the drive shaft into reciprocating vertical motion of the dildo.

The container includes a base portion, a top surface to mount a seat for the rider and a top surface to mount a seat for the partner, a hinged door in the rider end of the container to allow easy access for the changing of the dildo, a securely fastened door to permit occasional access to the motor means at the partner end. The motor is positioned within the container and is securely fastened to the base portion. The shape and dimensions of the container are such that the rider may comfortably straddle the seat and rest knees and feet upon the floor. The container is carried by grasping the portions of the rider and partner seats that extend beyond the length of the container. A roller is also provided to assist moving the container for short distances.

The motor includes an electric motor which turns a drive shaft. A gear box is interposed between the electric motor and the drive shaft for translating a high rate of rotation of the electric motor into a slower rate of rotation of the drive shaft. Electrical power extends from a power source through the container, through a ground fault circuit interrupter, through an on/off switch and indicator light, through a rheostat to the electric motor. The rheostat is used to vary the speed of the electric motor, the on/off switch to start or stop motion, the indicator light to indicate that electrical power is bring supplied to the electric motor, and the ground fault circuit interrupter is included as a safety device for the rider and partner in the event of a short circuit.

Means for selectively coupling the first end of the pivoting arm to the gear box includes a hub attached to the drive shaft. The hub has a rotating arm securely attached which has numerous apertures linearly spaced from the center of the hub. A link arm is loosely attached to the rotating arm by means of a ball joint rod end. The balljoint rod end is attached to another ball joint rod end by a threaded rod. The second ball joint rod end is attached to the first end of the pivoting arm.

Means for causing the pivoting arm to pivot about a point approximately midway along the length of the pivoting arm is provided by a male studded ball joint rod end connecting the pivoting arm to the support column. The support column is securely fastened to the base of the container.

Alternative means for causing the pivoting arm to pivot about a point approximately midway along the length of the pivoting arm is provided by a bolt passes through an aperture in the pivoting arm and a support column. The column is securely fastened to the base of the container.

Means of coupling the dildo to the second end of the pivoting arm is provided by a dildo mounting assembly. The dildo mounting assembly consists of a threaded locking collar, dildo girth adaptor ring, threaded coupling, connecting tube, and reinforcement collar. The dildo mounting assembly is loosely attached to the second end of the pivoting arm. The dildo girth adaptor ring may be exchanged with other girth adaptor rings thus providing a means to allow for the use of various girth dildos. The threaded coupling has a slotted opening beginning at the threaded end thus providing a means to allow for the exit of a wire when used with a wire remote controlled dildo. The threaded coupling and connecting tube are attached together by means of a cotter pin through a plurality of aligned holes in both the threaded coupling and the connecting tube. The cotter pin serves two purposes. The first purpose is to join the threaded coupling and the connecting tube with a means of quick disconnection, the second is to provide a means of preventing some slim dildos from falling through the dildo mounting assembly and making contact with the pivoting arm. The connecting tube and its surrounding reinforcement collar are provided with several vertically spaced holes which are aligned on opposing sides of the tubes. This arrangement provides a means of adjusting the effective length of the dildo mounting assembly which effects the starting penetration depth and ending penetration depth of the dildo attached to the threaded locking collar end of the dildo mounting assembly. Through one set of these holes, a bolt is passed. Midway through the interior of the connecting tube and its surrounding reinforcement collar the bolt passes through a hole in the second end of the pivoting arm, thus providing a means of loosely attaching the dildo mounting assembly to the pivoting arm. The pivoting arm being provided with several horizontally space holes provides a means of adjusting the position of the dildo forward and backward in the container. These horizontally space holes also provide a means of adjusting the length of reciprocating stroke imparted to the dildo. Because the pivoting arm is a lever with its fulcrum positioned between the two ends, a change in length of the pivoting arm on one side of the fulcrum (the support column) will cause the length of movement of the pivoting arm on one side of the fulcrum (the support column) to be shortened or lengthened. Repositioning the dildo mounting assembly closer to the support column will decrease the length of stroke and repositioning the dildo mounting assembly farther away from the support column will increase the length of stroke. Changing the hole in the rotating arm that the linng arm in attached to also provides a means of adjusting the length of stroke imparted to the dildo.

BRIEF DESCRIPTION OF THE SEVERAL VIEWS OF THE DRAWINGS

The accompanying drawings illustrate the invention. In such drawings:

FIG. 6 is an enlarged, exploded elevational view of the dildo mounting tube and dildo, as shown on FIG. 5, illustrating the adjustable depth that a dildo can be mounted inside the dildo mounting tube, illustrating the screw on dildo holding ring, illustrating the interchangeable dildo adaptor inserts, and illustrating the method that the remote control wire of the dildo exits the dildo mounting tube, and illustrating the flexible method of mounting the dildo mounting tube assembly to the;

DETAILED DESCRIPTION OF THE INVENTION

Figure 1:
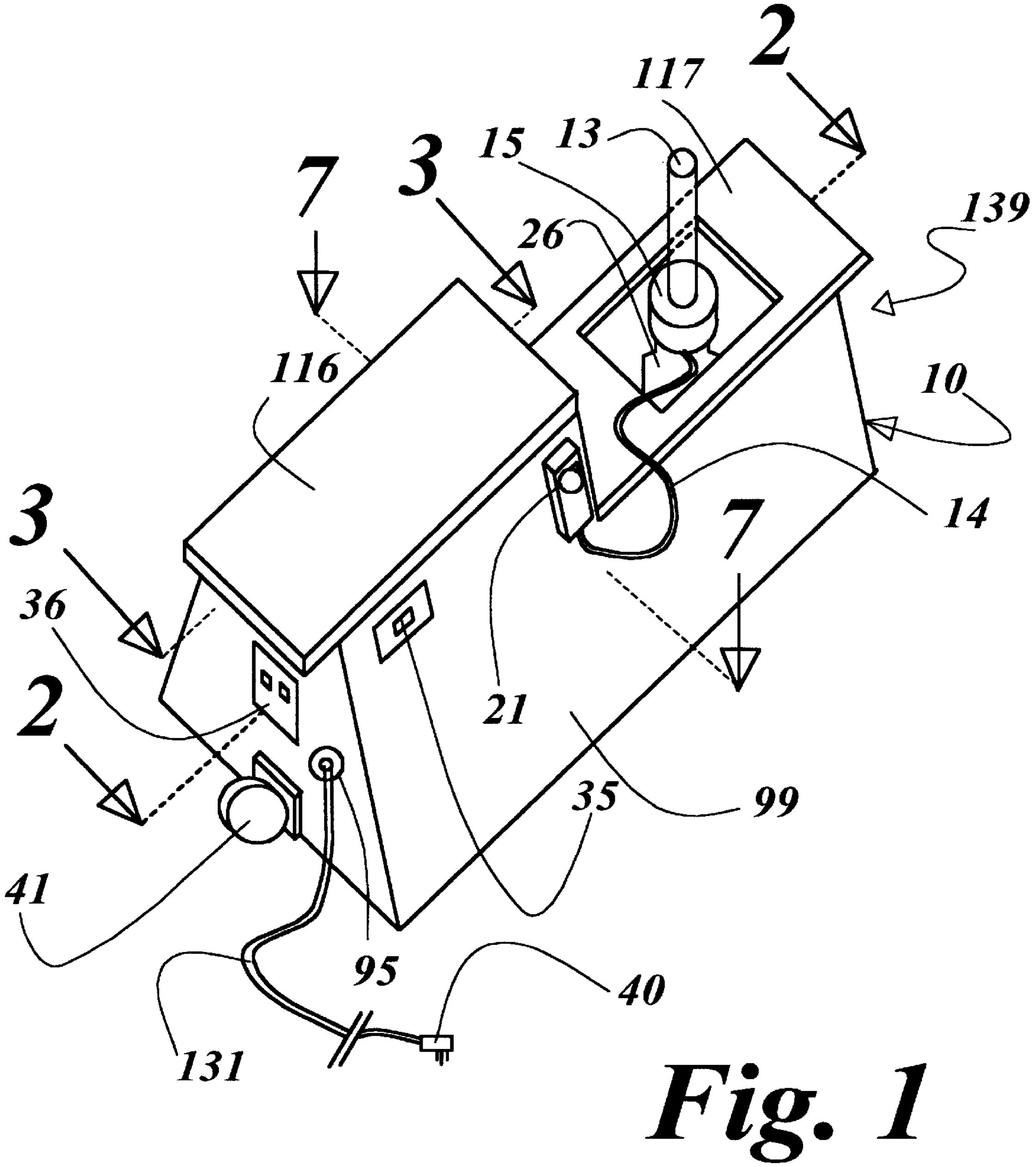
FIG. 1 is a perspective view of a preferred form of the sexual stimulation apparatus and shown assembled with a wire controlled vibrating dildo for vaginal stimulation of a woman.
Figure 2:
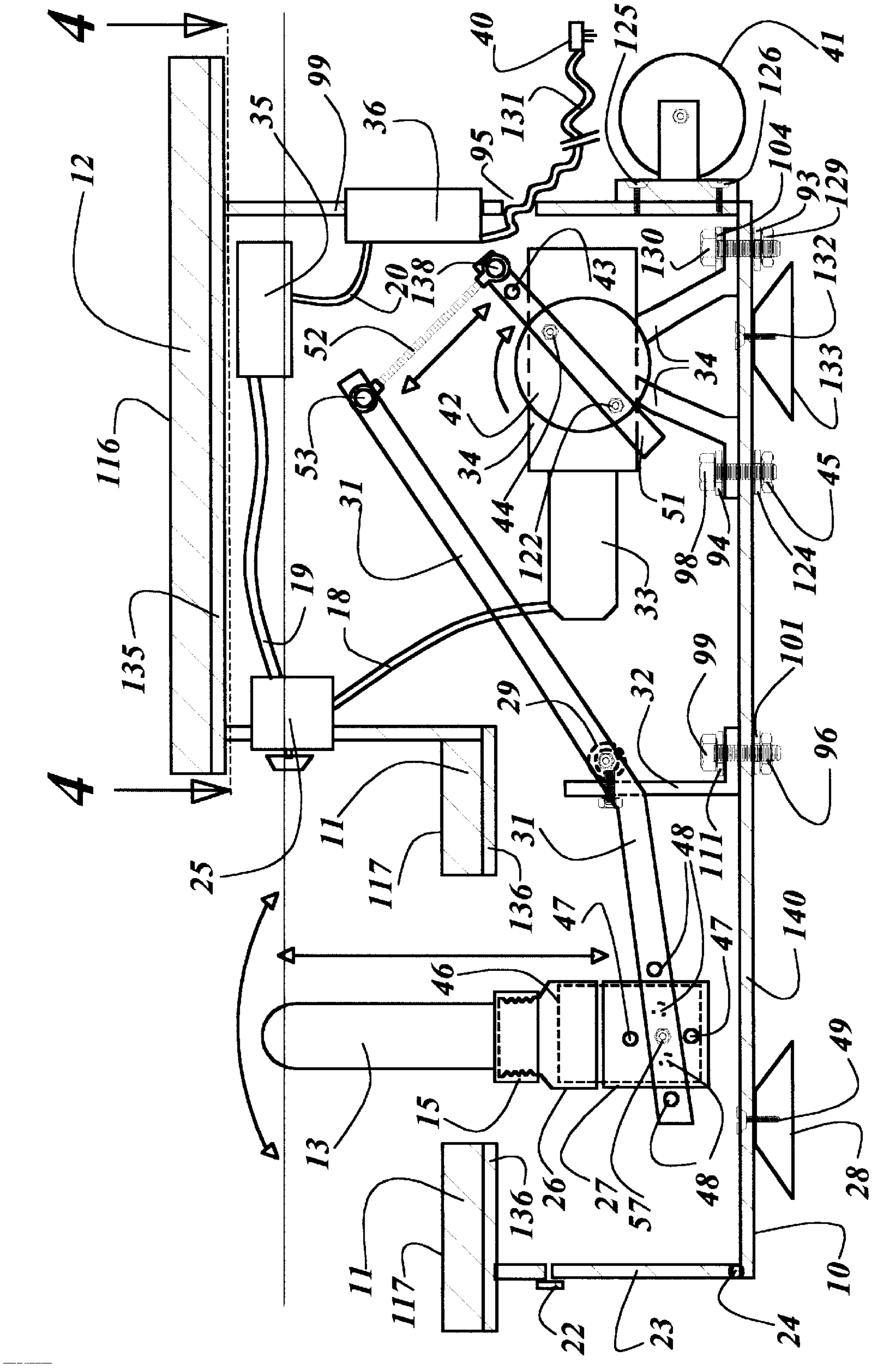
FIG. 2 is an enlarged fragmented vertical section taken generally along line 2—2 of FIG. 1, illustrating the interior of the container, and specifically the manner in which the pivoting arm is coupled to the motor.

As shown in the drawings for purposes of illustration, the present invention is concerned with a novel sexual stimulation apparatus generally designated by the reference number 139 (FIG. 1). In accordance with the present invention, and as illustrated with respect to a first embodiment in FIGS. 1 through 7, the stimulation apparatus 139 includes a box-like container 10 (FIG. 1). The container having a base portion 140 and two lids, 136 and 135 (FIG. 2). The container 10 is constructed of rigid members 99 (such as wood or plastic) connected together in such a manner as to give the container strength and rigidity (FIG. 2). The exact shape of the container may vary from a tube to a rectangular box (FIG. 2). The access door 23 is held in place by latch 22 and attached to the base 140 by hinge 24 (FIG. 2). The rider seat 117 and partner seat 116 are made by coating the tops 136 and 135 respectively with a suitable covering (such as leather or vinyl) (FIG. 2). Padding in the form of foam rubber 11 and 12 may be included (FIG. 2). The lids are extended beyond the ends of the container 139 for use as handles (FIG. 2). Seat 1 1 has an opening through which the dildo 13 and remote control wire 14 pass (FIG. 1). The dildo remote control unit/battery pack 21 is attached to the side of the container 10 with glue. A caster 41 is attached to the container by screw 125 and 126 (FIG. 2). Rubber pads 28 and 133 are attached to the base 140 by screw 49 and 132 (FIG. 2). Two other pads are not shown.

Figure 4:
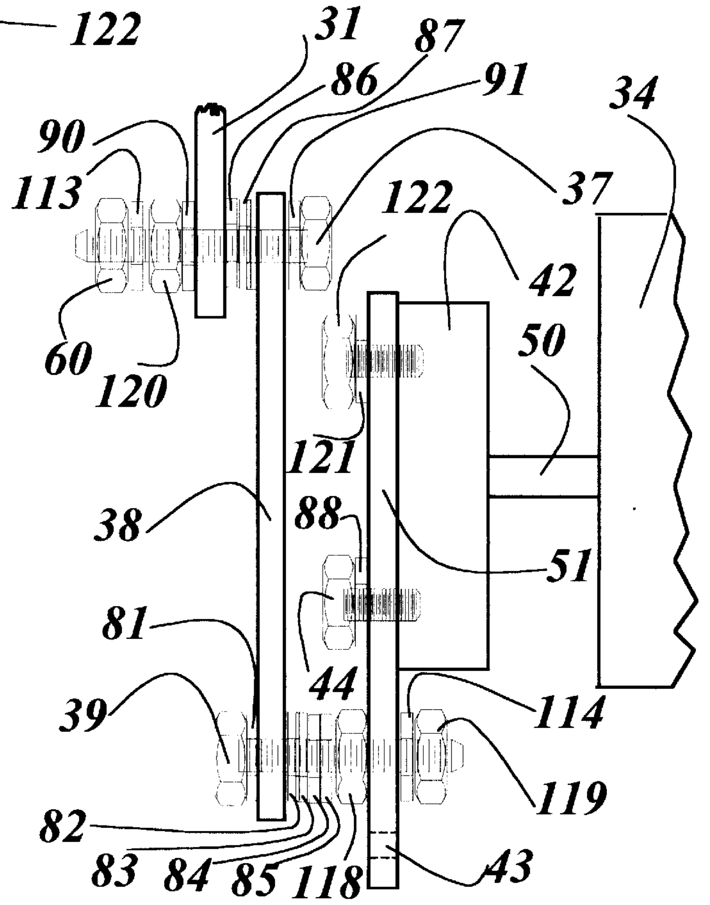
FIG. 4 is a detailed view of the elongated arm and the rotating arm, pivoting arm, and hub, taken generally along line 4—4 of as shown in FIG. 3, illustrating the alternative method of utilizing nuts, bolts and washers to substitute for the ball joint rod ends.

A gear reduction motor comprised of an electric motor 33 and its gear reduction unit 34 is attached securely to the base 140 by bolts 98 and 130 with flat washers (94, 124, 93, and 104) and self locking bolts 45 and 129 (FIG. 2). The output of the gear reduction unit 34 is a drive shaft 50 (FIG. 4). This arrangement desirably translates the high rate of rotation of the motor into the slower rate of rotation of the drive shaft. Power cable 131 extends from a power source (not shown) through the hole 95 (FIG. 2). Electrical power extends from a power source (not shown) through the container at hole 95, through a ground fault circuit interrupter 36, along wire 20, through an on/off switch and indicator light 35, along wire 19, through a rheostat 25, along wire 18, to the electric motor 33 (FIG. 2). The power cable 131 and cable end 40 are of the three connector type to provide power and a safety ground (FIG. 2). The rheostat 25 is used to vary the speed of the electric motor 33, the on/off switch 35 to start or stop motion, the indicator light (toggle of switch 35 contains a light) to indicate that electrical power is being supplied to the electric motor 33 even when the rheostat 35 has slowed the electric motor 33 to or below a point where the torque electric motor 33 can no longer overcome the combined resistance of the gear reduction unit 34, and the ground fault circuit interrupter 36 is included as a safety device for the rider and partner in the event of a short circuit (FIG. 2).

Figure 3:
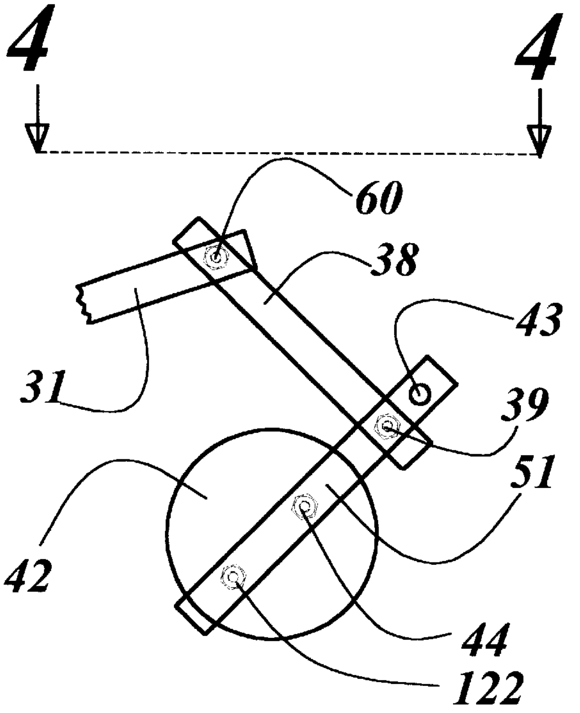
FIG. 3 is an enlarged elevational view of the elongated arm and the rotating arm, and hub, taken generally along line 3—3 of FIG. 1, illustrating the use of an alternative elongated arm constructed of a solid metal bar and bolts instead of ball bearing rod ends.

The rotational power from the drive shaft 50 is transferred to hub 42 (FIG. 4). The preferred method is to connect the link arm 52 directly to the hub 42 by use of a female studded ball joint end, thus eliminating parts 51, 122, 44, 121, and 88. Alternately, rotating arm 51 is secured to the hub with bolts 122 and 44, and lock washers 121 and 88 (FIG. 4). Rotating arm 51 is connected to the pivoting arm 31 with a link arm 52 made of a threaded rod (FIG. 2). The ends of the threaded rod have female studded ball joint ends 53 and 138 (FIG. 2). These ball joints are tightly fastened to the arms with nuts and lock washers (not shown). In a second alternative, a flat bar can be used to make the link arm 38 (FIG. 3). It is connected loosely to the rotating arm 51 by a bolt, washer and nut assembly that tightly locks bolt 39 to rotating arm 51 with nuts 118 and 119 and lock washer 114 (FIG. 4). Bolt 39 does not prevent the movement of link arm 38 because flat washers 81, 82, 83, 84, and 85 are not held tightly by bolt 39 (FIG. 4). This also provides a means to prevent link arm 38 from contacting bolts 121 and 44 (FIG. 4). Several holes 43 in the rotating arm 51 provide for a means of adjusting the effective radius of the hub 42 (FIG. 4). On the opposite end of link arm 38 a similar nut, bolt, washer assembly is used (FIG. 4). This combination differs in that the bolt does not tightly grip either the link arm 38 or the pivoting arm 31 (FIG. 4). This is done by nuts 60 and 120 tightened together against lock washer 113 (FIG. 4). The washers 90, 86, 87, and 91 are to allow bolt 37 to turn freely (FIG. 4). Either construction of arms converts the rotational movement of the hub 42 into a generally vertical and reciprocating movement of the pivoting arm 31 (FIG. 4). The number of flat washers may be adjusted to help align the linkage arms if the flat bar method is used (FIG. 4)

The pivoting arm 31 has a pivot point approximately half way between the link arm 52 and the dildo mounting assembly (FIG. 2). The two ends of a male studded ball joint rod end 29 are secured to the pivoting arm 31 and a metal angle 32 by self locking nuts (FIG. 2). This male studded ball joint rod end 29 functions as the pivot point for the pivoting arm. The two threaded ends of the male studded ball joint rod end 29 are at right angles to each other as seen in FIG. 2. When the link arm 52 pulls or pushes the end of the pivoting arm 31, the dildo mounting assembly end (all of FIG. 5) of the pivoting arm 31 is forced in the opposite direction (FIG. 2). Metal angle 32 is fastened to base 140 by bolt 99, self locking nut 96 and flat washers 111 and 101.

Figure 7:
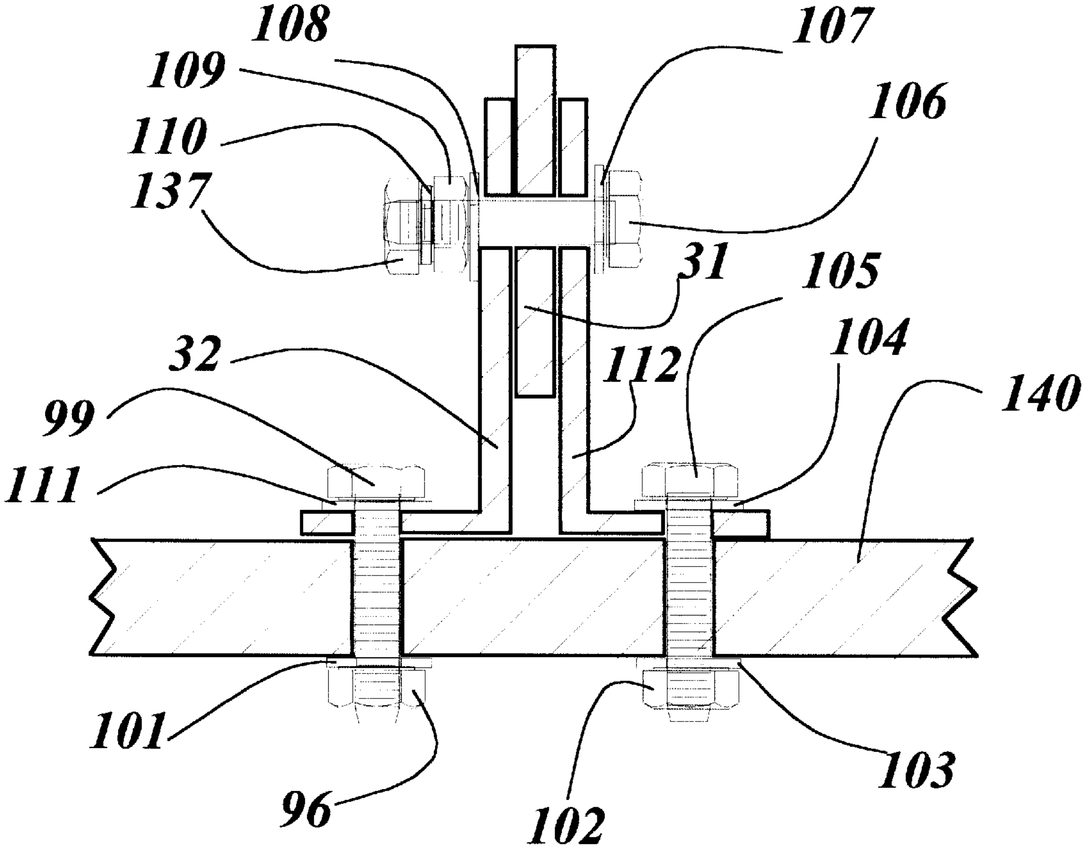
FIG. 7 is an enlarged, detailed view of the alternative method of constructing a pivot point of bolts, nuts and washers instead of a ball bearing rod end.

The alternate method of constructing the pivot point is by attaching two metal angles 32 and 112 to the base 140 with bolts 105 and 99, and self locking nuts 96 and 102 (FIG. 7). Flat washers 101, 103, 111, and 104 are also used (FIG. 7). Bolt 106 passes through a hole in metal angles 32 and 112 (FIG. 7). Nuts 137 and 109 are securely tightened with lock washer 110 (FIG. 7). Flat Washers 108 and 107 provide a surface for the nut and bolt to rotate on (FIG. 7). Pivoting arm 31 is loosely held between the two metal angles 32 and 112 (FIG. 7). Bolt 106 is the fulcrum of a simple lever and pivoting arm 31 is the lever (FIG. 7). When the link arm 52 pulls or pushes the end of the pivoting arm 31, the dildo mounting assembly (all of FIG. 5) end of the pivoting arm 31 is forced in the opposite direction (FIG. 2).

Figure 5:
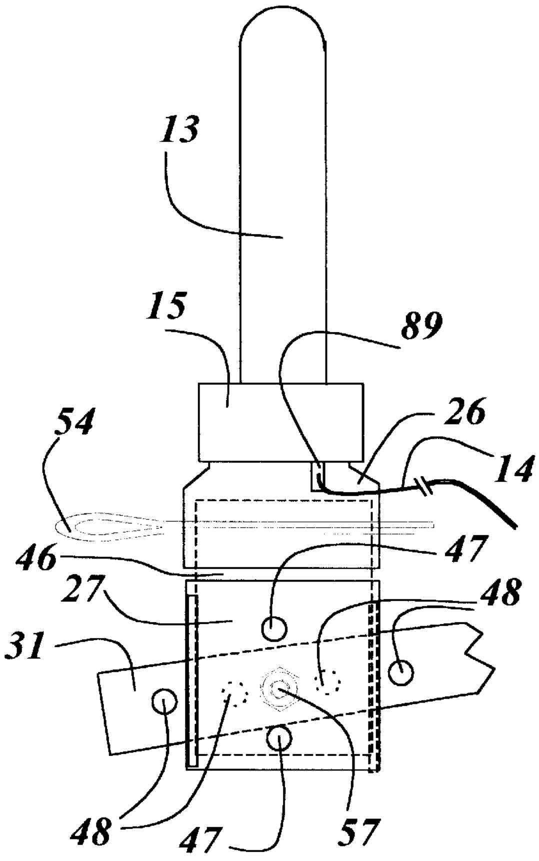
FIG. 5 is an enlarged elevational view of the pivoting arm and the dildo mounting tube, as shown in FIG. 2, illustrating the adjustable vertical position of the dildo mounting tube, and illustrating the horizontally adjustable length of the pivoting arm.
Figure 6:
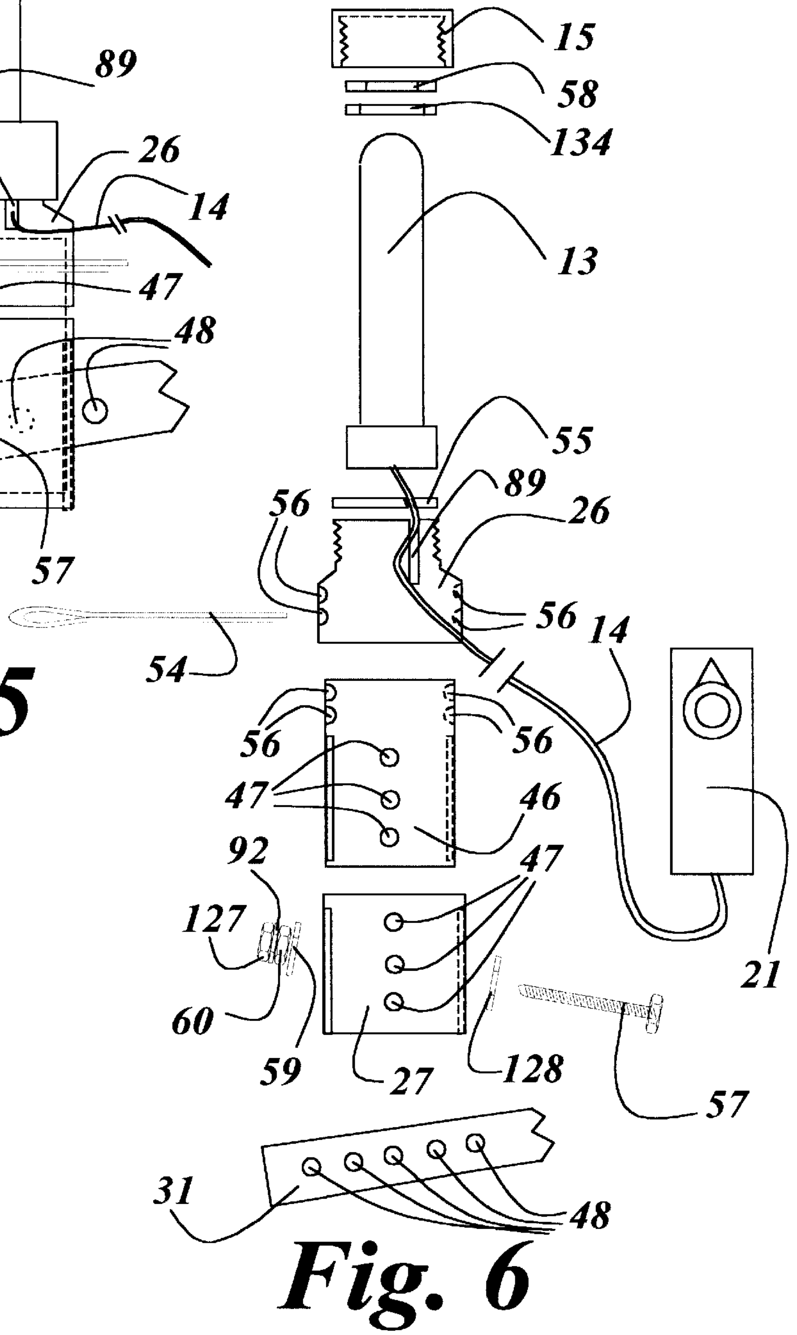

The dildo mounting assembly (all of FIG. 5) is attached to the pivoting arm 31 by one of several holes 48 in the arm (FIG. 2). The holes allow for adjusting the position of the dildo mounting assembly (all of FIG. 5) and its attached dildo 13 forward or rearward in the container 10 to meet the rider's needs (FIG. 2). The connecting tube 46 and its surrounding reinforcement tube 27 are attached by use of a bolt or quick disconnect pin through one of holes 47 to provide a means of adjusting the effective length of the dildo mounting assembly and therefore the starting depth of penetration of the dildo 13 and the final depth of penetration of the dildo 13 in the rider (FIG. 5). Midway through the connecting tube, the bolt or quick disconnect pin passes through one of holes 48 in the pivoting arm 31 (FIG. 5). In the alternative method where a bolt is used, the bolt is allowed to turn freely by using two nuts 60 and 127 and a lock washer 92 to prevent the bolt from falling from the dildo mounting assembly (FIG. 6). Flat washers 59 and 128 allow the bolt 57 to turn freely (FIG. 6). Slots cut vertically in the for and aft of the combination of the reinforcement tube 27 and the connecting tube 46 allow the pivoting arm 31 to pass through (FIG. 5). This also allows the dildo mounting assembly (all of FIG. 5) and it's attached dildo 13 to freely pivot on bolt 57 forward and rearward in relationship to the hole in the rider's seat 11 (FIG. 2).

The connecting tube 46 and its surrounding reinforcement tube 27 are connected to the threaded coupling 26 by means of a cotter pin 54 passing through one set of holes 56 that align on the three parts (FIG. 6). This provides a means of quick disconnect of the upper half of the dildo mounting assembly from the lower half (FIG. 6). The threaded coupling 26 has a slot 89 cut through the threaded area so that the remote control wire 14 of the dildo 13 may exit the threaded coupling 26 when the threaded locking collar 15 is in place (FIG. 6). Round plate 55 has a slot cut in it from the outside edge toward the center to allow for the passage of the remote control wire 14 (FIG. 6). The round plate 55 prevents the dildo 13 from falling through the center of the dildo mounting assembly (FIG. 6). The dildo 13 is shown in the preferred form of a wire remote controlled dildo (FIG. 6). Non wire remote controlled and non vibrating dildos may also be used. The only limitation is the threaded locking collar 15 and dildo girth adaptor ring 58 or 134 or none must fit over and around the dildo 13 (FIG. 6). Dildo girth adaptor rings 58 or 134 or none are used to adapt the dildo to snugly fit inside the threaded locking collar 15 which in turn is screwed onto the threaded collar 26 to complete the dildo mounting assembly and dildo combination (FIG. 6).

From the foregoing it is to be appreciated that the novel sexual stimulation apparatus 139 is powered by ordinary household electrical current, is lightweight and can be carried about freely, is easy to clean, and store. The fact that the dildo 13 can be of various girths, lengths, shapes, and textures allows this machine to be of use to both men and women. Although the drawings and detailed descriptions have been used to illustrate a box like container, a tube of plastic may be substituted.

I claim:

1. A sexual stimulation apparatus, comprising:

a rectangular box-like housing provided with a hole in its top;

a gear reduction motor (the common name for a single-unit electric motor and gearbox) for translating the high rate of rotation of the electric motor into the slower rate of rotation of an output shaft of the gearbox;

a controlling device as a means of controlling the electricity supplied to the gear reduction motor;

a hub connected to the output shaft of the gearbox of the gear reduction motor to provide a means of attaching items to the output shaft;

a rotating arm with several holes along the length of the rotating arm, radially attached to the hub to provide a means of attaching a linking arm at several distances from the center of the hub thereby simulating various diameter hubs;

the linking arm as a means of coupling the rotating arm to the first end of a pivoting arm in a manner that translates the rotational motion of the hub and the rotating arm into the vertical reciprocating motion of the pivoting arm;

a pivoting arm in a generally horizontal orientation, with holes along the length of the pivoting arm, having the first end coupled to the lining arm and the second end coupled to a dildo mounting assembly;

a pivot point approximately in the middle of the pivoting arm as a means of causing the pivoting arm to pivot and thereby imparting reciprocating vertical motion to the dildo mounting assembly end of the pivoting arm in an opposite direction than the pivoting arm was pulled or pushed by the linkage arm;

the dildo mounting assembly being generally vertical in orientation to provide a means of fastening various dildos to the pivoting arm;

seats for the rider and a partner, the rider seat being positioned so that the dildo extends through a hole in the seat, the partner seat being positioned so that the rider and partner may kiss, hug, and caress each other as the machine sexually stimulates the rider and the partner operates the controls.

2. The sexual stimulation apparatus of claim 1 further comprising a controlling means for varying the speed of the electric gear reduction motor provided by a rheostat.

3. The sexual stimulation apparatus of claim 1 further comprising a light which indicates if electrical power is being supplied to the motor.

4. The sexual stimulation apparatus of claim 1 further comprising a ground fault interrupt circuit which is placed in a electrical system of the apparatus to protect the rider and partner from electrical shock.

5. A sexual stimulation apparatus of claim 1 in which the hub has a securely attached arm, called the rotating arm, which is radially attached to the hub with several holes along the length of the rotating arm to provide a means of adjusting the placement of the linkage arm, effectively changing the diameter of the hub and thereby changing the amount of displacement of the pivoting arm caused by the rotation of the hub, a displacement that determines the depth of stroke of a dildo.

6. The sexual stimulation apparatus of claim 1 further comprising the use of flexible, resilient material to construct the pivoting arm provides a means for firm yet yielding attachment of the dildo mounting assembly to the gear reduction motor and the hub eliminating the need for guides to prevent excessive sideways movement of the dildo mounting assembly.

7. The sexual stimulation apparatus of claim 1, further comprising rubber pads fastened to the underside of the rectangular, box-like housing in order to isolate a floor on which the sexual stimulation apparatus is placed from the vibrations of the sexual stimulation apparatus.

8. A sexual stimulation apparatus of claim 1 in which the top of the rectangular box-like housing is extended forward and rearwards to form handles at each end for carrying.

9. The sexual stimulation apparatus of claim 1, further comprising a roller or caster on one end of the rectangular box-like housing and a handle on the opposite end by which the apparatus may be moved without lifting.

10. The sexual stimulation apparatus of claim 1 in which holes along the length of the generally horizontal pivoting arm provide various points to attach the dildo mounting assembly thereby providing a means of adjusting a stroke length of the dildo mounting assembly by changing the ratio of the effective length of the pivoting arm on the dildo mounting assembly end of the pivoting arm to a fixed length of the pivoting arm on the linking arm end of the pivoting arm.

11. The sexual stimulation apparatus of claim 1, further comprising a commercially available vibrating dildo attached to the dildo mounting assembly adapted to stimulate a rider.

12. The sexual stimulation apparatus of claim 11 further comprising mounting means attached to the side of the sexual stimulation apparatus, said mounting means adapted to hold a remote control for the commercially available vibrating dildo within reach of a rider and partner.

13. The sexual stimulation apparatus of claim 1 in which the link arm has ball joint bearings on each end to provide a means of reducing friction when attaching the lining arm to the rotating arm and the pivoting arm.

14. The sexual stimulation apparatus of claim 1, further comprising a screw cap, having a hole through a center of the screw cap, for a dildo to extend through, providing a means of clamping the dildo into the dildo mounting assembly.

15. The sexual stimulation apparatus of claim 14, further comprising adaptor rings, adapted to be placed around the dildo, which are held in place by the screw cap, to secure various girth dildos.

16. The sexual stimulation apparatus of claim 1 further comprising a slot in the dildo mounting assembly provides a means for the exit of a remote control wire of the dildo.

17. The sexual stimulation apparatus of claim 1 in which the dildo mounting assembly is flexibly attached to the pivoting arm by a bolt passing in through a hole in the lower half of the dildo mounting assembly, then through a hole in the pivoting arm and then out through a hole in the dildo mounting assembly thereby allowing the tilting of the dildo mounting assembly forwards and rearwards in the sexual stimulation apparatus to self adjust to an internal vaginal or anal angle of a rider.

18. The sexual stimulation apparatus of claim 1 in which excessive sideways tilting of the dildo mounting assembly is prevented by passing the pivoting arm into, through, and out of slots in the forward and rearward walls of the dildo mounting assembly.

19. The sexual stimulation apparatus of claim 1 further comprising a base plate located under the dildo to prevent smaller dildos from dropping through the dildo mounting assembly and making contact with the pivoting arm.

20. The sexual stimulation apparatus of claim 1 further comprising holes along the vertical length of the dildo mounting assembly to provide a means of attaching the dildo mounting assembly to the pivoting arm in such a way as to raise or lower the dildo on the pivoting arm, thus adjusting the starting depth and final depth the dildo can penetrate into a rider.

21. The sexual stimulation apparatus of claim 1 further comprising a cotter pin used to fasten together the overlapping upper and lower halves of the dildo mounting assembly to allow for quick separation of the upper and lower halves of the dildo mounting assembly thus providing a means of easily removing the upper half of the dildo mounting assembly from the sexual stimulation apparatus for cleaning the dildo and upper half of the dildo mounting assembly.

22. The sexual stimulation apparatus of claim 21 in which the length of the dildo mounting assembly can be changed by fitting the overlapping upper and lower halves of the dildo mounting assembly together by passing the cotter pin through different aligned sets of vertically positioned holes in the two halves, thus providing a means of adjusting the starting depth of the dildo and the ending depth of the dildo in a rider.

23. The sexual stimulation apparatus of claim 1 in which the pivot point utilizes ball bearings to reduce friction.

* * * * *